United States Patent [19]

Nice et al.

[11] Patent Number: 5,547,940
[45] Date of Patent: Aug. 20, 1996

[54] METHOD FOR STIMULATING PROLIFERATION OF COLON CELLS USING POMC$_{76-103}$

[75] Inventors: Edouard C. Nice; Robert James; Richard J. Simpson; Antony W. Burgess, all of Parkville; Robert H. Whitehead, Victoria, all of Australia

[73] Assignee: Ludwig Institute for Cancer Research, New York, N.Y.

[21] Appl. No.: 202,525

[22] Filed: Feb. 28, 1994

Related U.S. Application Data

[63] Continuation-in-part of Ser. No. 851,732, filed as PCT/US92/02492, Mar. 16, 1993, Pat. No. 5,316,937.

[51] Int. Cl.$^6$ .......................... A61K 38/00; A61K 35/55; C12N 5/00
[52] U.S. Cl. .......................... 514/21; 514/2; 435/240.2; 435/240.21; 435/240.3; 435/240.31; 424/565
[58] Field of Search .......................... 435/240.2, 240.3, 435/240.31, 240.21; 424/565; 514/2, 21

[56] References Cited

U.S. PATENT DOCUMENTS 5,316,937  5/1994  Whitehead .......................... 435/240.3

OTHER PUBLICATIONS

Whitehead, et al, "A Colon Cancer Cell Line (LIM 1215) Derived From a Patient With Inherited Nonpolyposis Colorectal Cancer", JNC1 74: 759–765.

Whitehead, et al, "A Method For The Isolation And Culture Of Human Colonic Crypts In Collagen Gels", In Vitro Cellular & Developmental Biology 23(6): 436–442 (Jun. 1987).

Whitehead, et al, "Detection of Colonic Growth Factors Using a Human Colonic Carcinoma Cell Line (LIM 1215)", Int. J. Cancer 46: 858–863 (1990).

Whitehead, et al, "A Method For The Prolonged Culture of Colonic Epithelial Cells", J. Tiss. Cult. Meth. 13: 103–106 (1991).

Nice, et al., "The Major Colonic Cell Mitogen Extractable From Colonic Mucosa Is an N–terminally Extended Form of Basic Fibroblast Growth Factor", J. Biol. Chem. 266(22): 14425–14430 (1991).

Fenger et al., J. Biochem. 250: 781–88 (1988).
Nakanishi et al., Nature, 278: 423–27 (1979).
Bateman et al, J. Biol. Chem., 265 (36): 22130–22136 (1990).
Moyer et al., Science, 225: 1445–47 (1984).
Cossu et al., Developmental Biology, 131: 331–336 (1989).
Bohlen et al., FEBS Lett., 128: 67–70 (1981).
Arola et al. Cell Tissue Res., 271 (1): 169–76 (1993).
Li, Lab. Invest., 8: 574–87 (1959).
Rubtsov et al., Mol. Biol., 19: 226–35 (1985).
Hughes et al, Nature, 258: 577–79 (1975).

Primary Examiner—Michael G. Wityshyn
Assistant Examiner—Susan M. Dadio
Attorney, Agent, or Firm—Felfe & Lynch

[57] ABSTRACT

The invention describes how known peptide POMC$_{76-103}$ can be used to stimulate colon cell proliferation. The peptide can be used alone, or in combination with other cell proliferation stimulating agents.

15 Claims, 12 Drawing Sheets

METHOD FOR STIMULATING PROLIFERATION OF COLON CELLS USING POMC$_{76-103}$

RELATED APPLICATIONS

This application is a continuation-in-part application of PCT Application PCT/US93/02492 filed Mar. 16, 1993, which is itself a continuation-in-part of U.S. patent application Ser. No. 851,732, filed Mar. 16, 1992 now U.S. Pat. No. 5,316,937.

FIELD OF THE INVENTION

This invention relates to a factor useful as a stimulator of cell proliferation, such as intestinal cells and colonic crypt cells. More particularly, it relates to the peptide having the amino acid sequence set forth in SEQ ID NO: 1 and uses thereof.

BACKGROUND AND PRIOR ART

Many cell products have been identified via analysis of their effect on targeted cell populations and subpopulations. Such products include a plethora of materials including growth factors, cytokines, and so forth. These substances are extremely powerful and are produced in vanishingly small amounts by normal cells.

One of the major goals of contemporary molecular biology is the identification and cloning of genes which produce the various materials generally discussed supra. While such genes have been identified for materials such as erythropoietin (see, e.g., U.S. Pat. No. 4,703,008), and interleukin-7 (see, e.g., U.S. Pat. No. 4,965,195), the relevant genetic material is not always available, or is not available as quickly as the art would like. In such cases, an important means of securing sufficient amounts of the material of interest is via the identification and isolation of cell lines which produce the desired product.

Examples of proteinaceous cell products which were first identified via cell lines which produced them are "granulocyte colony stimulating factor" or "G-CSF" (see U.S. Pat. No. 4,833,127), and interleukin-3 (see U.S. Pat. No. 4,658,018). The latter patent is of particular interest because, while the factor could not be completely characterized in terms of parameters such as molecular weight, isoelectric point, etc., its functional properties were clearly defined. Another example of this approach to factors of biological pertinence and their isolation from cell lines may be seen in Golde et al., U.S. Pat. No. 4,438,032. Of course, the artisan is also aware of the vast number of known monoclonal antibodies which are produced by hybridoma cell lines. Frequently, the most pertinent feature of these proteins is their specificity, and this is all that is required to identify them.

Although many factors involved in the formulation of cell growth have been identified, the diversity of different cell types is evidence of the need to continue work toward identifying and characterizing factors which have specific targets, i.e., which stimulate particular cell types.

The different cell types of a mature organism do not appear "sua sponte", rather, they develop from precursor cells which have the ability to self renew and to differentiate into different types of mature cells. These precursor cells are referred to as "stem cells" generally, and are an important resource to the field for studies on cellular development. The importance of stem cells to basic research can be seen in U.S. Pat. No. 5,061,620, to Tsukamoto et al., which involves the isolation and maintenance of hematopoietic stem cells. Various media, including IMDM, and RPMI are described as growth media which can be used to maintain these stem cells.

The stem cells which develop into colonic mucosa are also referred to as colonic crypt cells or as a population thereof. While it has been possible to isolate these cells from mixed culture, their cultivation has been difficult. See in this regard Whitehead et al., In Vitro Cellular and Developmental Biology 23(6): 436–442 (1987), hereinafter referred to as "In Vitro", the disclosure of which is incorporated by reference. The methodology described therein requires, inter alia, the use of collagen gels and feeder layers of bovine aortic cells for extended culture of the crypt cells. This methodology is involved, and not completely satisfactory for the cultivation of colonic crypt cells.

Tumor cells are frequently the source of cell lines which are high producers of stimulatory factors for their normal counterparts. With reference to the patent literature cited supra, e.g., the cell lines identified as producers of G-CSF and IL-3, e.g., were isolated from tumorous material.

Cell lines derived from colon tumors and which can be traced to colonic crypt cells are known, as per, e.g., Whitehead et al., JNCI 74(4): 759–762 (1985), the disclosure of which is incorporated by reference and which described cell line LIM 1215, whose origin is traced to colon crypt cells. Not all cell lines produce pertinent factors, however, and there is no guarantee or pattern as to which cell lines will produce a stimulatory factor.

Previous investigations yielded a cell line which produces a membrane associated factor not otherwise recognized by the art, and which acts as a mitogen on colonic crypt cells. The factor acts as a mitogen in that it stimulates DNA synthesis and proliferation of the targeted cells (i.e., colon crypt cells). The factor is secreted by the producing cell line into the growth medium, to yield a conditioned medium which stimulates proliferation of colonic crypt cells. It is this mitogen, the cell line producing it, and applications thereof, which were the subject of the parent and grandparent applications of the parent case. These two applications disclosed, in FIG. 5, and in example 8, the use of crude pituitary material "A2". This material is an extract of bovine pituitary glands, and has been shown to be a potent clonogen for colonic carcinoma cell line LIM 1215. See, e.g., Whitehead et al., J. Nat. Canc. Ins. 74:759–765 (1985). The fraction, as indicated, is crude; however, pituitary extracts have been stuided further and it has been found, surprisingly, that the peptide consisting of the amino acid sequence of SEQ ID NO: 1 is a powerful stimulator of colonic carcinoma cell proliferation. It is this aspect of the peptide which is the basis for the invention described herein.

Figure 1:
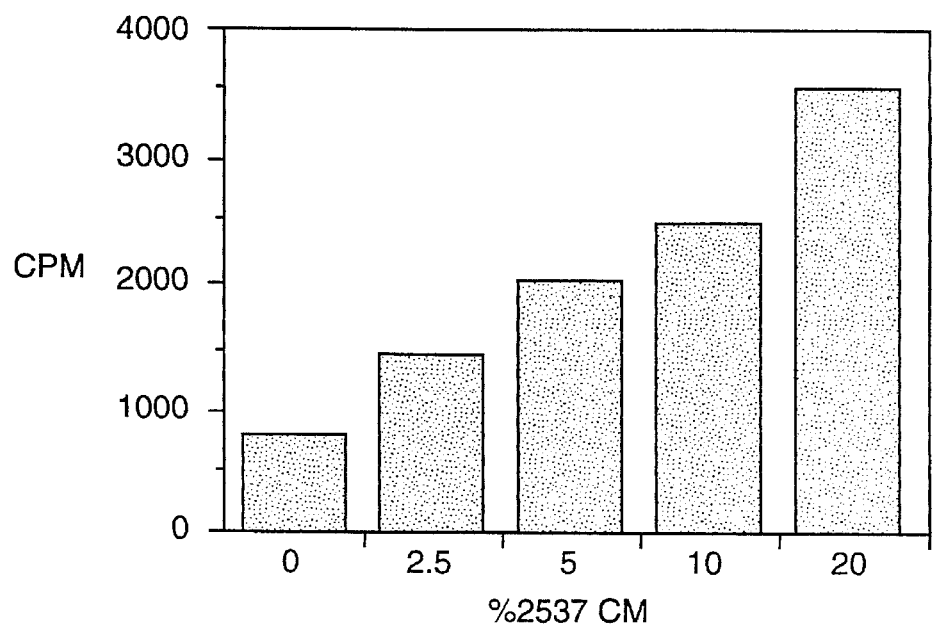
FIG. 1 shows incorporation of radiolabelled thymidine into human colon crypt cells, when cultured in the presence of mitogen from LIM 2537.

DETAILED DESCRIPTION OF THE
PREFERRED EMBODIMENTS

EXAMPLE 1

The cell line LIM 2537 was established from a biopsy taken from a human colon tissue sample.

A polyp lying adjacent to a colonic carcinoma in the rectum was observed to possess unusual features in that an excess number of nerve fibers and blood vessels were observed.

A portion of the polyp was used to establish cultures following the protocols described by Whitehead et al., JNCI, supra, the disclosure of which is incorporated by reference. After about two months of slow growth in culture, a small cell variant was noted which overgrew all cells in the culture. Cells of this variant were passaged, and stored in liquid $N_2$ at a low passage level. In addition, they were capable of growth in RPMI 1640 containing 5% fetal calf serum (FCS), and could be harvested using a trypsin-EDTA solution for later passage. Cells grew as small spindle shaped cells with numerous rounded cells either loosely attached or floating in medium. The clones also grew in semi-solid agar using standard techniques. Cloning efficiency increased markedly as cell concentration increased, indicating an autocrine effect.

Studies showed that the cells grew readily as xenografts in nude mice, forming palpable tumors within 19 days. The cells are aneuploid, having about 55–60 chromosomes. They stain with anti-keratin monoclonal antibody LE-61, indicating they are of epithelial origin. They do not stain with anti-mucin antibodies or with antibodies to brush border markers other than aminopeptidase N.

A cell line has been established from the described culture, and has been named LIM 2537. A deposit of the cell line has been made in accordance with the Budapest Treaty on Apr. 8, 1993 at the European Collection of Animal Cell Cultures, PHLS Centre for Applied Microbiology and Research, Porton Down, Salisbury Wits, SP4, CJG, United Kingdom. Accession Number is ECACC 92040800.

EXAMPLE 2

The autocrine effect observed supra suggested that a factor was produced by the cells and secreted into the medium. As such, conditioned medium was prepared and then used in subsequent tests, described infra.

A sample of LIM 2537 cells was grown to 75% confluency, following the cultivation protocol described supra. Medium was then changed to RPMI 1640 plus 2% fetal calf serum (FCS), and followed by incubation for 48 hours at 37° C. Medium was collected, filtered through a 0.22µ sterile filter, and stored at −70° C. until tested.

EXAMPLE 3

The effect of the conditioned medium described in Example 2 on colonic crypt cells was tested.

A piece of normal colonic mucosa was washed and sterilized by soaking in a 0.1% solution of sodium hypochlorite in phosphate buffered saline (PBS) for 20 minutes at room temperature. Colonic crypt cells were then removed by using a solution containing 3 mM EDTA plus 0.5 mM DTT, as described by Whitehead et al., In Vitro 23: 436–442 (1987).

The mucosa was incubated for 90 minutes at room temperature, the EDTA mixture removed, and PBS was then added. The resulting mixture was then shaken vigorously to free crypts from the remaining tissue. This step was repeated until the yield of crypts decreased. The resulting crypt suspension was centrifuged gently, and the crypts were suspended in RPMI 1640 plus 5% fetal calf serum. Crypt concentration was adjusted to 300 crypts per ml, and the suspension aliquoted into wells of 24 well culture dishes, in 1 ml volume.

The LIM 2537 culture medium described supra was thawed and added to labelled wells at concentrations of from 2.5% to 20% (v/v), followed by incubation at 37° C. for 48 hours. Tritiated thymidine was then added to the wells at a concentration of 1µ Curies per well, and incubation continued for another 6 hours. The cells' DNA was harvested on glass fiber paper using a commercial harvester, and the papers were then placed in a liquid scintillation vial, to which scintillation fluid was added. Vials were counted in a liquid scintillation counter, and tritiated thymidine incorporation equal to at least twice that of tube background was considered indicative of background activity.

The results obtained are shown in FIG. 1. It is clear from these data that the conditioned medium contains a factor which is stimulating the proliferation of colonic crypt cells in a concentration dependent manner.

EXAMPLE 4

The experiments set forth in Example 3 involved human crypt cells. Parallel experiments were carried out, using colons from both new born and adult mice. Colons were removed from the mice, opened longitudinally, contents removed, and the colons were then washed in PBS, followed by the same steps set forth in Example 3.

Figure 2:
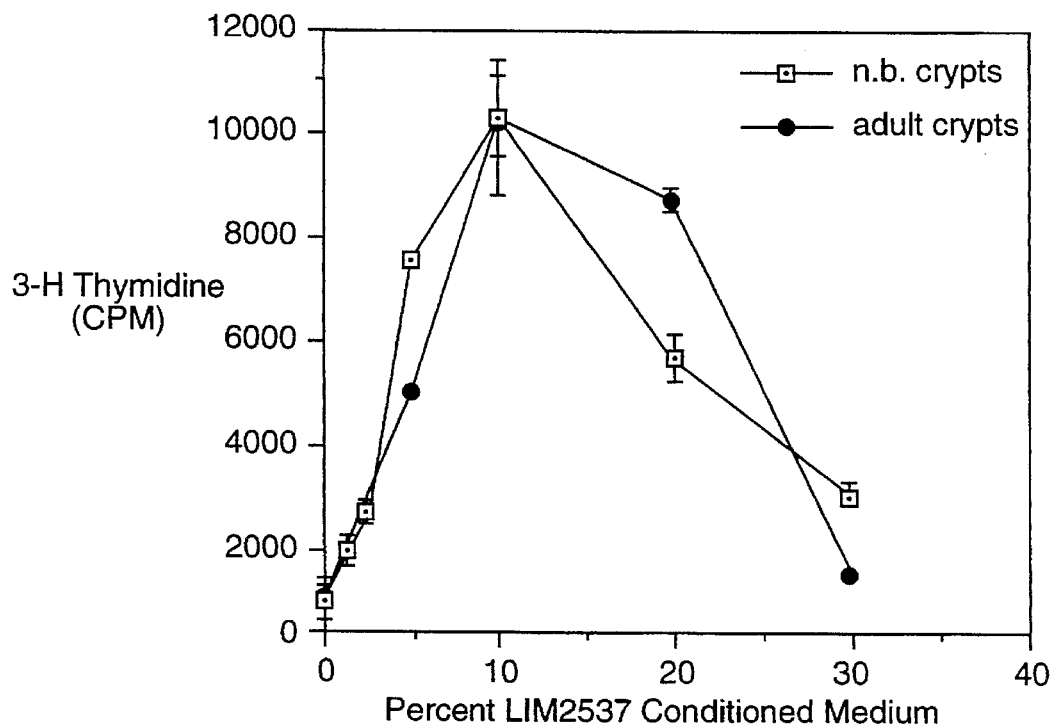
FIG. 2 depicts stimulation of murine colon crypt cells at various concentrations of conditioned medium containing the LIM 2537 mitogen.

FIG. 2 presents these results. It is noted that similar data were obtained with both newborn and adult colonic crypt cells.

EXAMPLE 5

Figure 3:
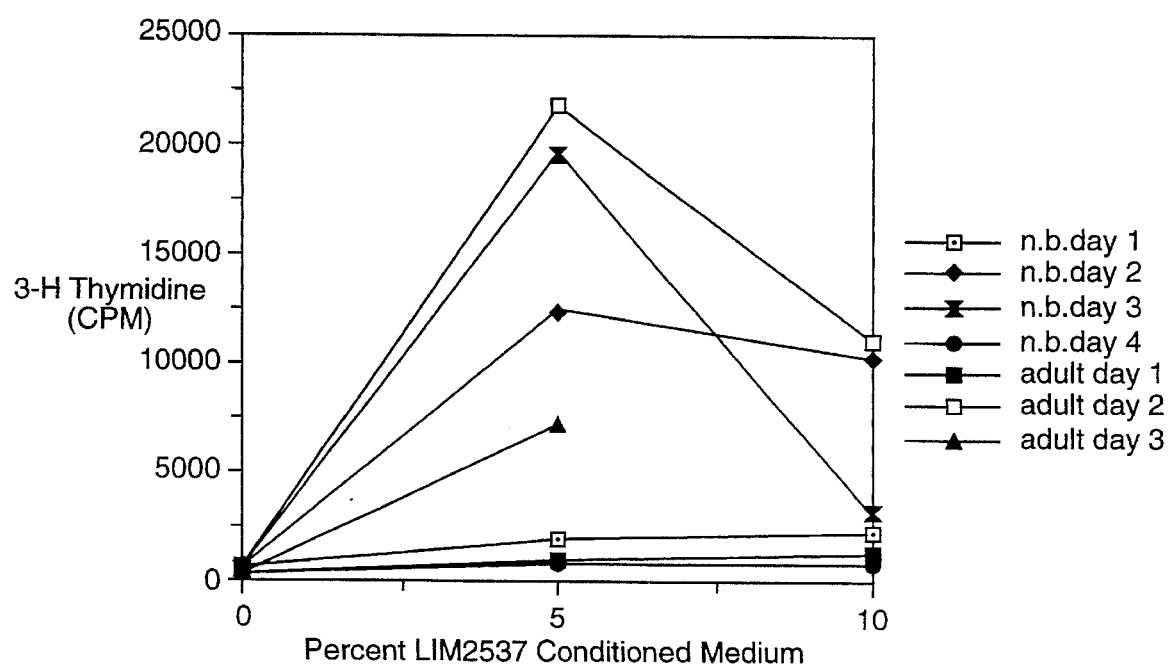
FIG. 3 presents results obtained when stimulation of murine colonic crypt cells in the presence of the mitogen was studied over time.

The same colonic crypt cell stimulation assay that was carried out in Example 4 was again performed, with the single exception that harvesting was after 48 hours. FIG. 3 sets forth these results, and indicates that while the degree of stimulation varied from assay to assay, especially with respect to optimal concentration of medium, the medium did induce DNA synthesis in the colonic crypt cells.

EXAMPLE 6

In another set of experiments, human colonic crypt cells were tested with conditioned medium from LIM 2537, together with different growth factors. Some of the growth factors tested included epidermal growth factor ("EGF"), fibroblast growth factor ("FGF"), interleukin 6 ("IL-6"), platelet derived growth factor ("PDGF"), gastrointestinal peptide "PPP", and glucagon. None of these factors showed any synergism with the LIM 2537 conditioned medium, when tested on murine colonic crypt cells.

EXAMPLE 7

Figure 4:
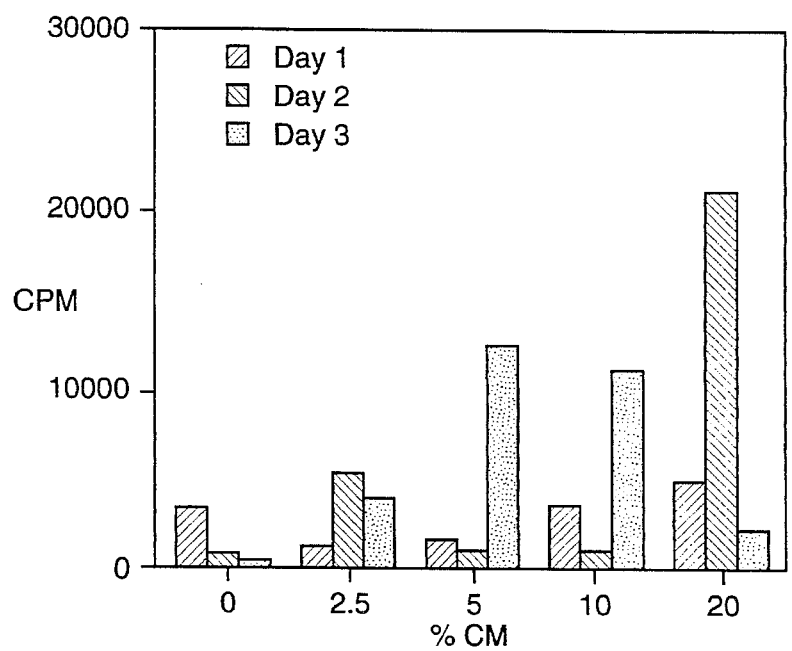
FIG. 4 shows the response of human colon crypt cells to LIM 2537 mitogen over time and at varying concentrations.

The response of human colonic crypt cells over time and at varying concentrations was also examined. FIG. 4 summarizes these results, which were secured using the thymidine incorporation assay described supra. Depending upon the concentration, stimulation was greatest on either the second or third day of culture; however, at all concentrations, the crypt cells were stimulated by the conditioned medium.

EXAMPLE 8

Colony formation using various factors was studied. Cells of cell line LIM 1215 were cloned in semi-solid agar (0.3%) following Whitehead et al., Int. J. Canc. 46:858–863 (1990). Briefly, the cells were trypsinized and resuspended in RPMI 1640 plus 5% FCS. Cells in the suspension were counted and then resuspended in a mixture of 0.3% agar in RPMI 1640 plus 10% FCS (40° C.), at a concentration of $10^4$ cells per ml. The mixture was plated in 1.5 volumes in 35 $mm^2$ dishes, and allowed to set. Plates were then incubated at 37° C. in 5% $CO_2$ and 100% humidity for 14 days. A solution of 0.1% crystal violet was aded to the plates, and colonies of more than 40 cells were counted.

Conditioned medium was prepared by incubating confluent monolayers of colon carcinoma cell lines with fresh RPMI 1640 plus 5% FCS for 48 hours. Medium was then removed, sterilized by filtration, and added to the agar plates at a final concentration of 10% (v/v). Basic fibroblast growth factor ("bFGF"), and a crude pituitary fraction, referred to as "A2" were also tested These materials had previously been shown to be active as colonic carcinoma cell growth factors. See Whitehead, supra.

Figure 5:
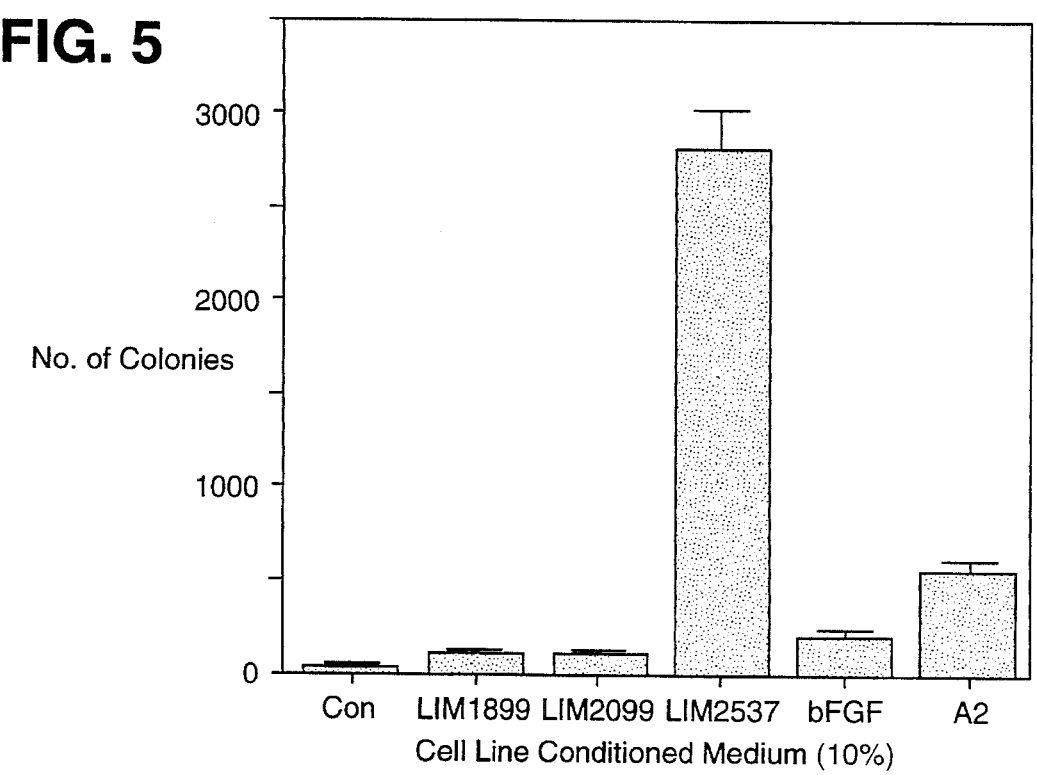
FIG. 5 shows data from a colony formation assay.

The results of these experiments are shown in FIG. 5. Note the vast superiority of the conditioned medium obtained from LIM 2537 as compared to other materials.

EXAMPLE 9

In another experiment, human colonic crypt cells were combined with an ammonium sulphate precipitate ("ASP") of the LIM 2537 conditioned medium.

Human crypts were isolated from colonic mucosa using 3 mM EDTA and 0.5 mM DTT, following Whitehead et al., In Vitro 23: 436–442 (1987). The crypt cells were resuspended in RPMI 1640 containing 2% FCS, and the concentration was then adjusted to 200 crypts per ml. The crypt suspension was aliquoted into the wells of 24 well plates in 1 ml volume. One hundred mls of conditioned medium were prepared from 48 hour cultures of LIM 2537, clarified by centrifugation, and ammonium sulphate was added to a final concentration of 30% (w/v). The mixture was allowed to stand for 4° C. overnight, and was then centrifuged. The supernatant was discarded, and the pellet resuspended in 10 mls of phosphate crypts in doubling dilutions, starting at 2%. LIM 2537 conditioned medium was also tested after freezing for 48 hours in order to test stability. Crypts were cultured at 37° C. for 48 hours, and were then labelled by adding $^3$H-thymidine at a final concentration of 1μ/Ci per ml. Plates were reincubated for six hours, and the cells were harvested onto glass fiber filter mats. Amounts of incorporated radioactivity was determined in a liquid scintillation counter.

Figure 6:
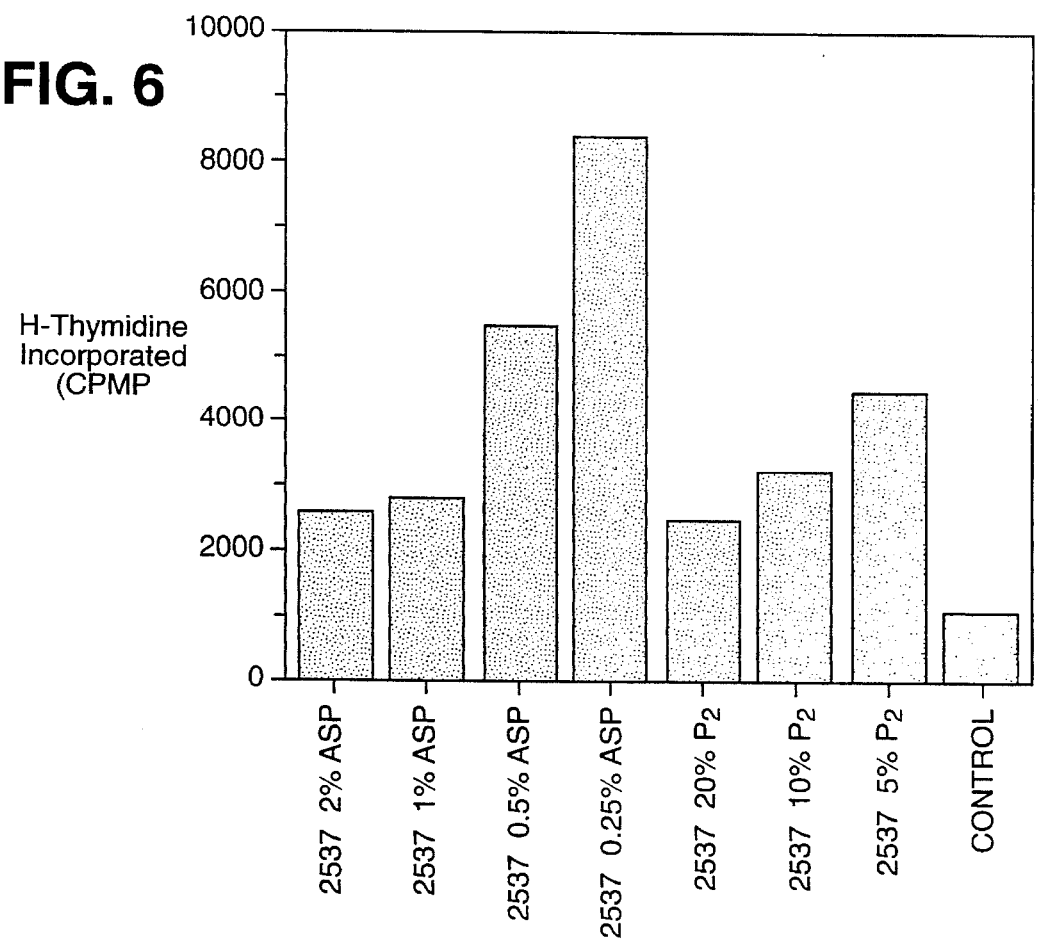
FIG. 6 compares LIM 2537 ammonium sulphate precipitates and frozen LIM 2537 conditioned medium at varying concentrations.

The results, shown in FIG. 6, depict the precipitate ("ASP") in the first four columns reading left to right, and the results with frozen material ("FZ") in columns 5–7, reading left to right. A control experiment is also shown. Again, the performance of the factor is clear.

EXAMPLE 10

A comparison was made among LIM 2537 conditioned medium, the precipitate, redissolved in PBS, or precipitate redissolved in TRIS.

Adult mouse colonic crypt cells were isolated from colonic mucosa, and were plated in 24 well plates at 200 crypts per well in RPMI 1640 plus 2% FCS. Conditioned medium was added at concentrations of 5, 10 and 20%, and after precipitation with ammonium sulphate. The precipitated material was either redissolved in phosphate buffered saline (PBS) (pH 7.2) or in PBS containing 20 mM TRIS (pH 7.2).

Figure 7:
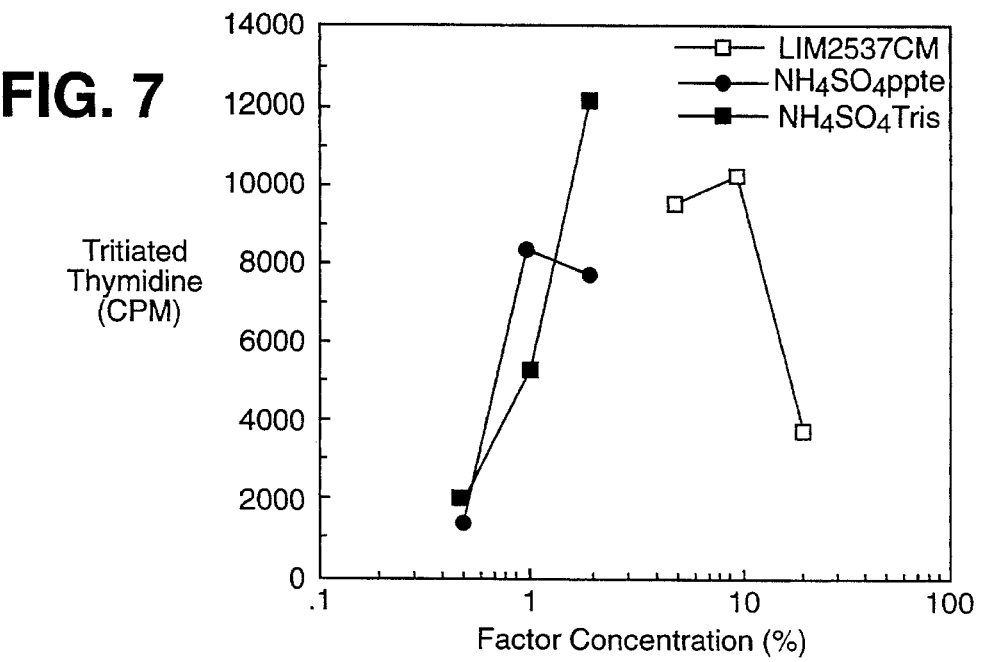
FIG. 7 displays data obtained from LIM 2537 conditioned medium, ammonium sulphate precipitate resuspended in phosphate buffered saline, and the resuspension with Tris buffer added.

FIG. 7 presents these results, with the TRIS solution clearly showing the best results. Control values are marked on the Y axis.

EXAMPLE 11

Figure 8:
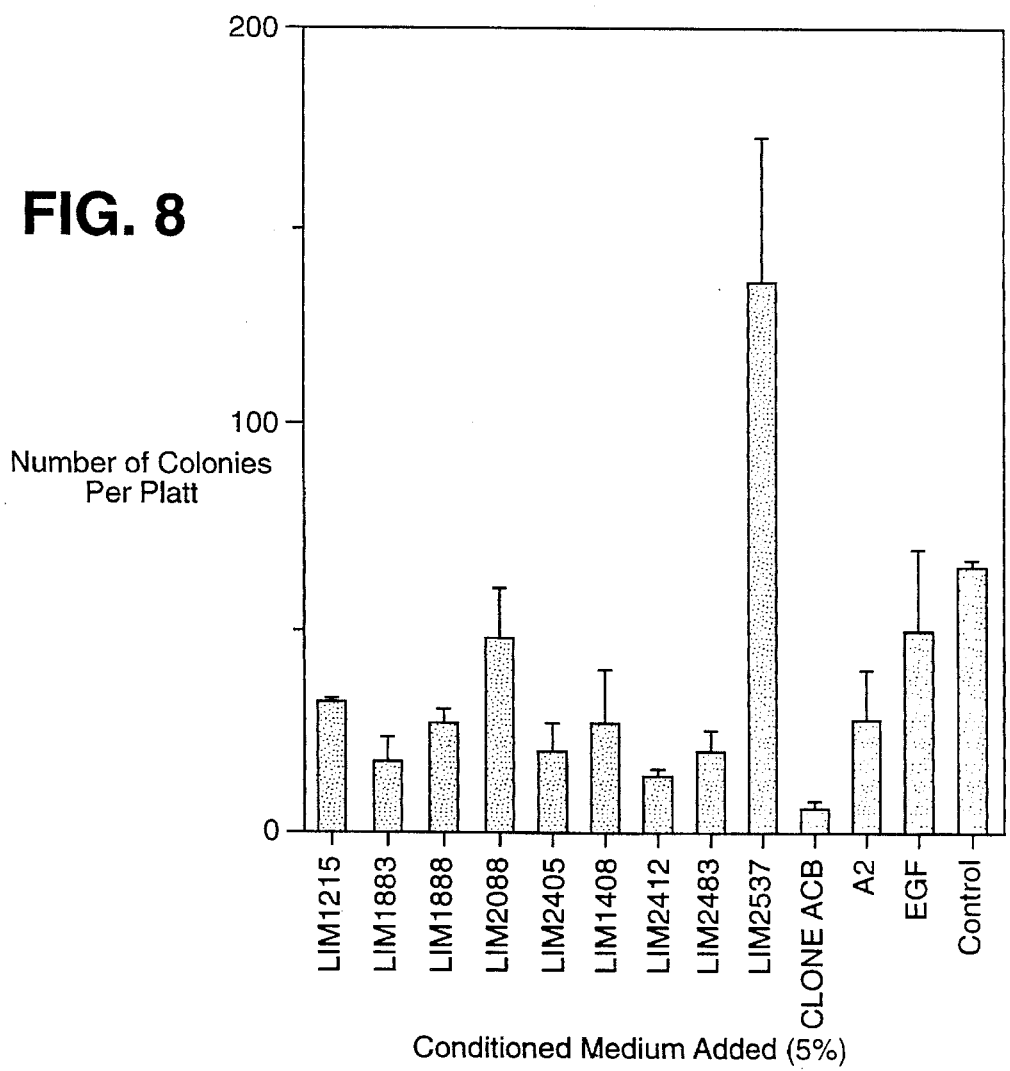
FIG. 8 compares the ability of a number of conditioned media from colonic crypt cell lines and various growth factors to induce colony formation of LIM 2405 cells in an agar assay. Included is A2, the peptide of the invention.

The LIM 2537 conditioned medium was tested for its ability to stimulate colony formation of other colon carcinoma cell lines, i.e. LIM 1215 and LIM 2405, described by Whitehead et al., J. Nat. Canc. Ins. 74: 759–765 (1985), and Whitehead et al., Immunol. Cell Biol. 70: 227–236 (1992), respectively. The cells were plated at final densities of 20000 cells/ml (LIM 2405). Conditioned media from various cell lines were tested, and the data are presented in FIG. 8. In addition, A2 and EGF were also tested. The clear superiority of LIM 2537 as compared to the other factors is evident.

EXAMPLE 12

Conditioned medium from LIM 2537 was tested in an assay, using normal mouse and human colonic mucosal crypt cells. Mouse colons were opened and washed with running water to remove fecal material, and surfaces were decontaminated using 0.04% sodium hypochlorite. Human colonic mucosa were obtained from colectomy specimens, and apparently normal tissue was taken from sites distant from tumors. Human tissue was washed in the same way as murine samples were washed. Crypts were isolated as described supra, and crypts were then aliquoted in 1 ml volumes into rat tail collagen coated 24 well plates at a concentration of 300 crypts per cell in RPMI 1640 plus 2% fetal calf serum. Any factor being tested was added in 0.1 ml volumes to triplicate wells, followed by incubation at 37° C., for 44 hours. Wells were labelled with 1μCurie/ml (final concentration) of $^3$H-thymidine for four hours. After this step, the contents of the wells were lysed, and harvested onto glass fiber filters before being counted in a beta counter, following Whitehead et al., Int. J. Cancer 46: 858–863 (1990). The factors EGF, b-FGF, KGF SCF (epidermal growth factor, basic fibroblast growth factor, keratocyte growth factor and stem cell factor), were used over a range of 1 ng/ml to 20 ng/ml, as were TGF-α and TGF-β.

Figure 9:
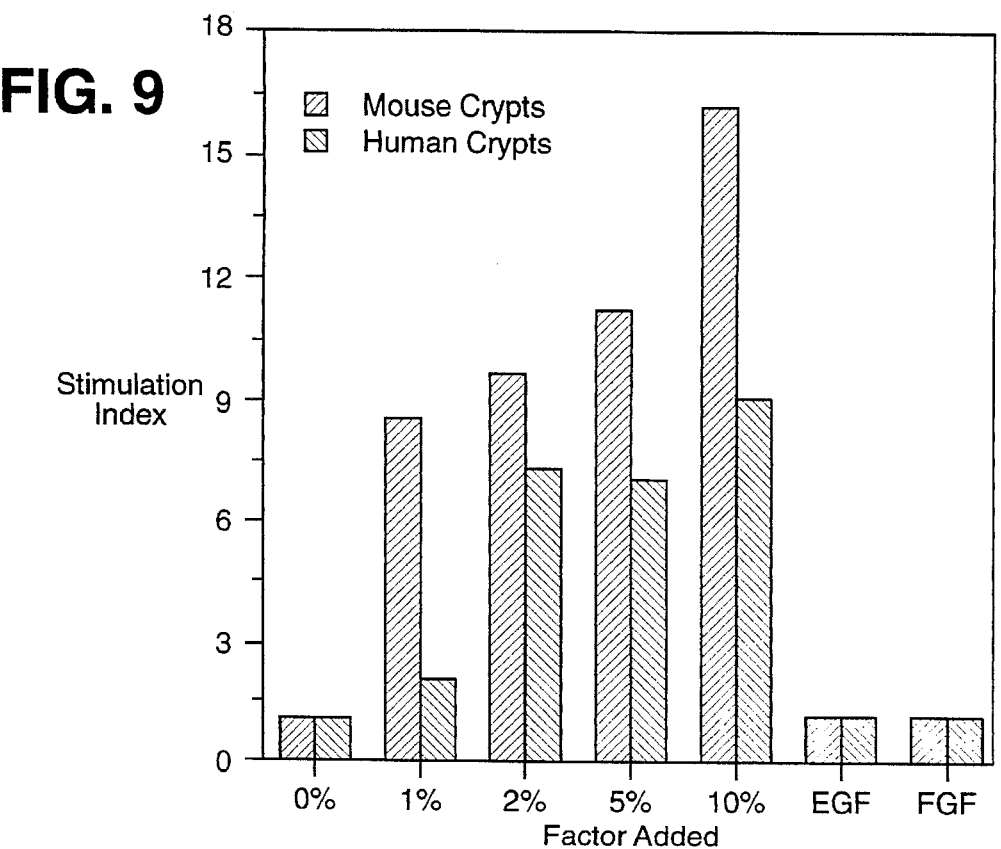
FIG. 9 compares conditioned medium containing the growth factor of the LIM 2531 cell line to the growth factors EGF and FGF.
Figure 10:
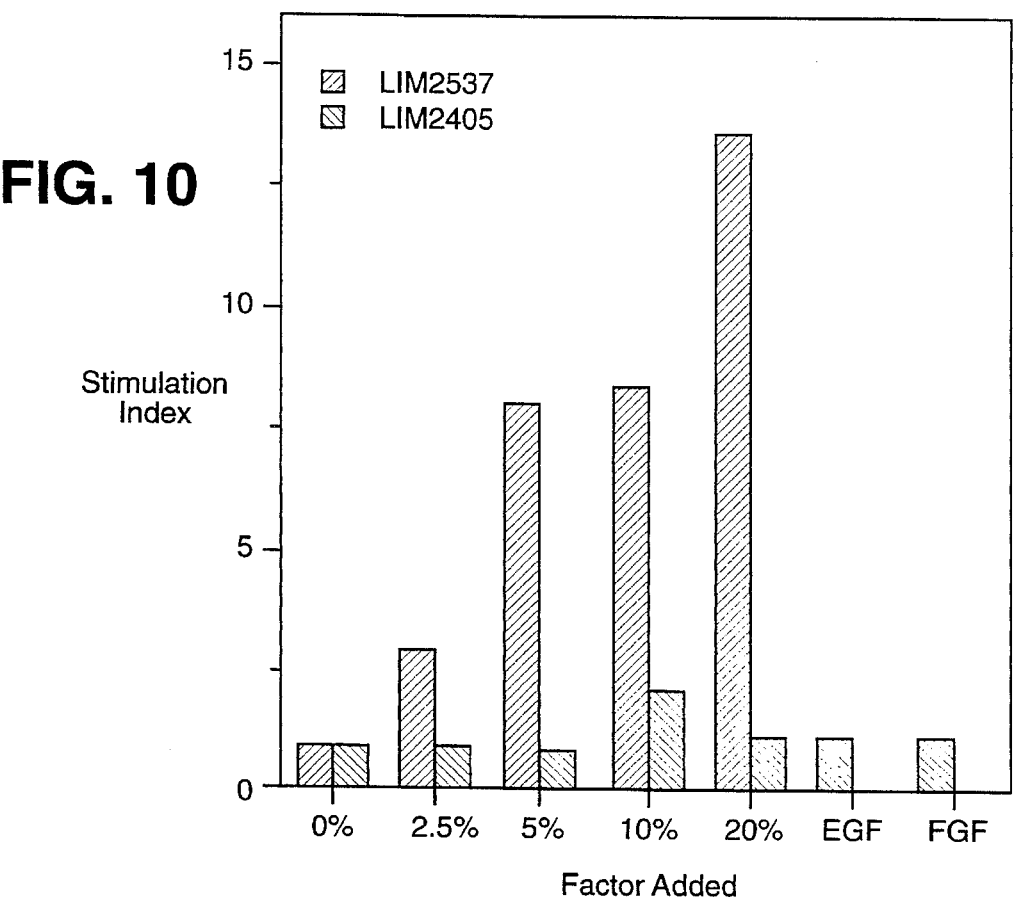
FIG. 10 compares the conditioned medium of the LIM 2537 cell line to a representative growth factor containing conditioned medium.

These results are set forth in FIGS. 9 and 10. FIG. 9 depicts the measurement of $^3$H-thymidine incorporation in crypt cells. The conditioned medium from LIM 2537 caused $^3$H-thymidine uptake, unlike either of EGF or FGF. Similarly, LIM 2405 conditioned medium did not stimulate uptake. Although the results are not shown, the other factors set forth supra, as well as conditioned media from cell lines LIM 1215, LIM 1839, LIM 2097, LIM 2415, and LIM 2408 were tested. None, with the exception of LIM 2408, showed any activity, and while LIM 2408 showed some, it did not approach that shown by LIM 2537.

The foregoing experiments demonstrate that cell line LIM 2537 produces a factor which is clearly mitogenic to colonic crypt cells. Further investigations have revealed that this factor is heat labile, and is only stable over a pH range of from 6 to 8.

In addition, samples of the conditioned medium were centrifuged at 10,000 rpm for 30 minutes to form a supernatant and membrane-containing pellet. The majority of the activity was found to be in the pellet, indicating that the factor is membrane associated. Electron micrographs of the pelleted materials has confirmed the presence of vesicles.

EXAMPLE 13

Figure 11:
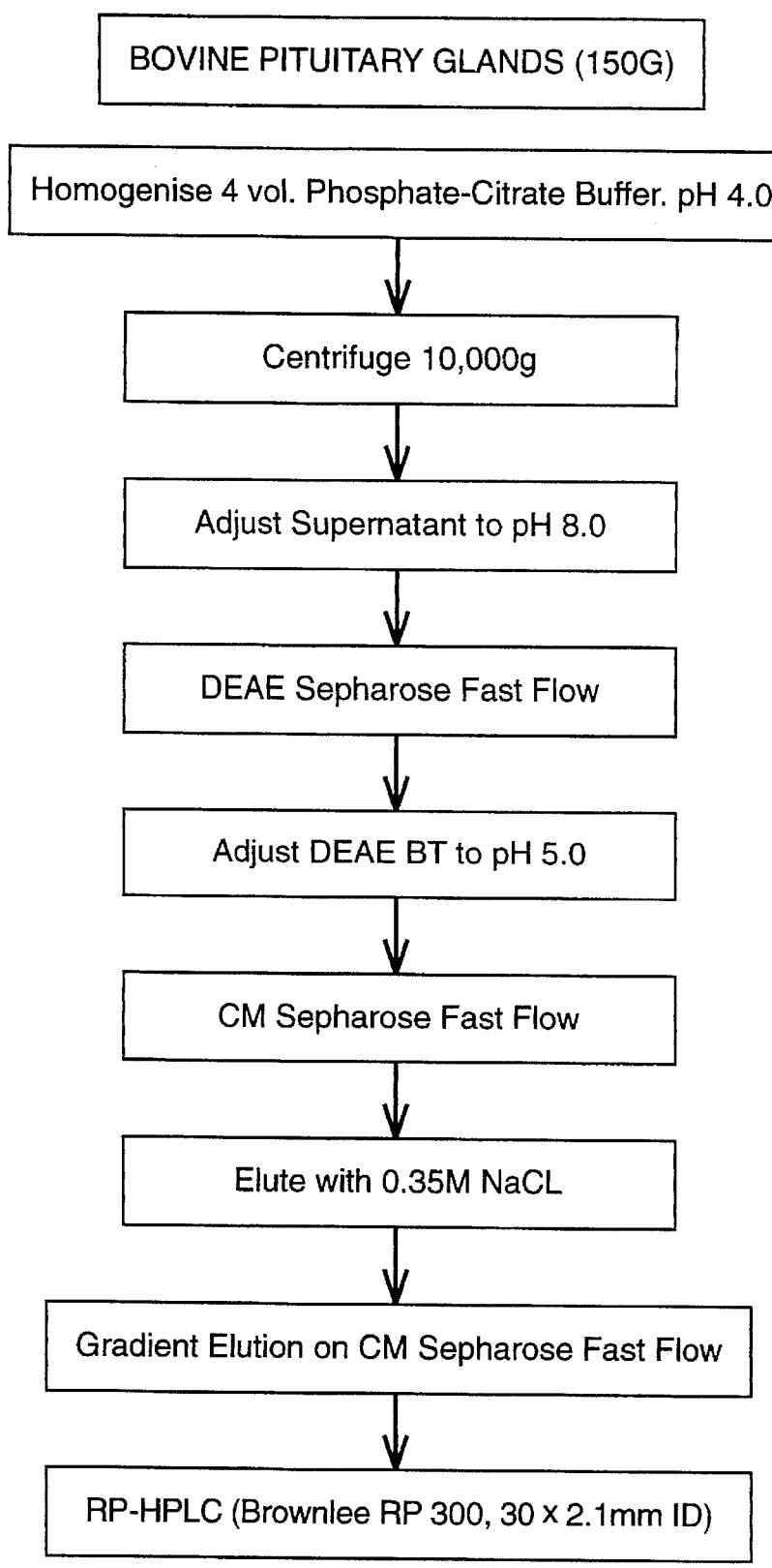
FIG. 11 is a summary of the purification protocol leading to the peptide used in the invention.
Figure 12:
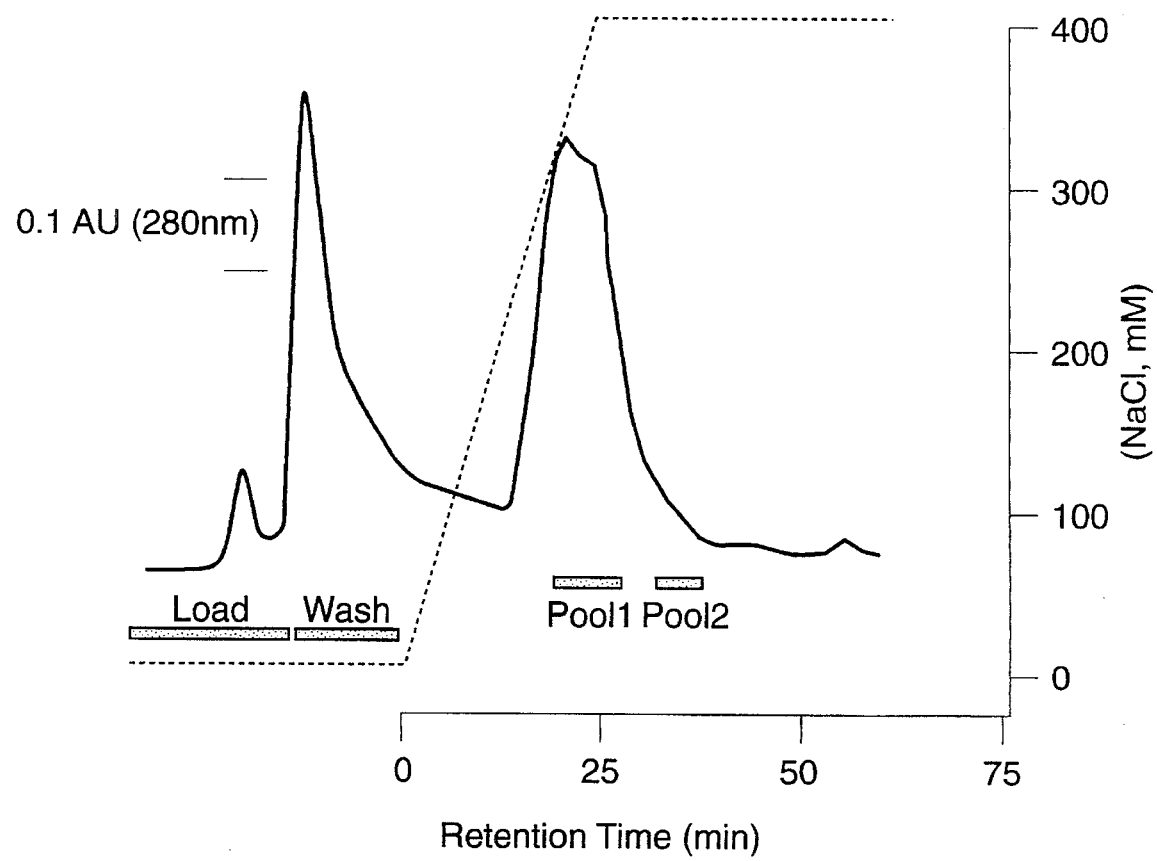
FIG. 12 depicts the results obtained following application of extract to a CM Sepharose Fast Flow column of reduced dimensions.

The A2 fraction of bovine pituitary glands (FIG. 11) and the method for its preparation have been disclosed previously, as per Smith et al., J. Cell Physiol 119: 320–326 (1993), and Smith et al., BBRC 119: 311–318 (1984), the disclosures of both of which being incorporated in their entirety. In addition to preparations of A2 made following these protocols, extracts of fresh, 150 g samples of bovine pituitary glands were homogenized in phosphate-citrate buffer (4 volumes, pH 4.0), and the supernatant was clarified by centrifugation at 10000 g. The resulting extracts were adjusted to a pH of 8.0 with 5M NaOH and loaded, at a flow rate of 50 ml/min, onto a DEAE Sepharose fast flow column (300×50 mm I.D.), at a temperature of 4° C. Breakthrough fraction contained LIM 1215 mitogenic activity, as shown by the examples and FIG. 5, supra. This fraction was adjusted to pH 5.0 with 1M HCl, and applied to a CM Sepharose Fast Flow column. The column was eluted stepwise, at a flow rate of 50 ml/min, with 0.1 and 0.35M NaCl in 20 mM ammonium acetate (pH 5.0)(240 ml fractions). An aliquot of the active, 0.35M fraction was diluted 1:3 with distilled water, adjusted to pH 5.0 by dropwise addition of 1M HCl, and concentrated and further purified by gradient elution at a flow rate of 2 ml/min (linear 25 min. gradient between 10 mM sodium phosphate (pH 5.0), and the same buffer containing 0.4M NaCl, followed by isocratic elution with the 0.4M NaCl buffer for a further 15 minutes) on another CM Sepharose Fast Flow column of reduced dimensions (i.e., 100×10 mM I.D.) FIG. 12 shows these results.

EXAMPLE 14

An aliquot (1 ml) of the peak active fraction (POOL 1) obtained in example 13, supra, was loaded onto a Brownlee Aquapore RP 300 reversed phase HPLC column (30×2.1 mm I.D.), and the column was eluted, at a flow rate of 100 ul/min, with a linear 60 minute gradient between 0.15% (v/v) aqueous trifluoroacetic acid (TFA) as primary solvent, and 60% aqueous acetonitrile containing 0.125% TFA (v/v) as secondary solvent. Column temperature was 45° C.

Figure 13A:
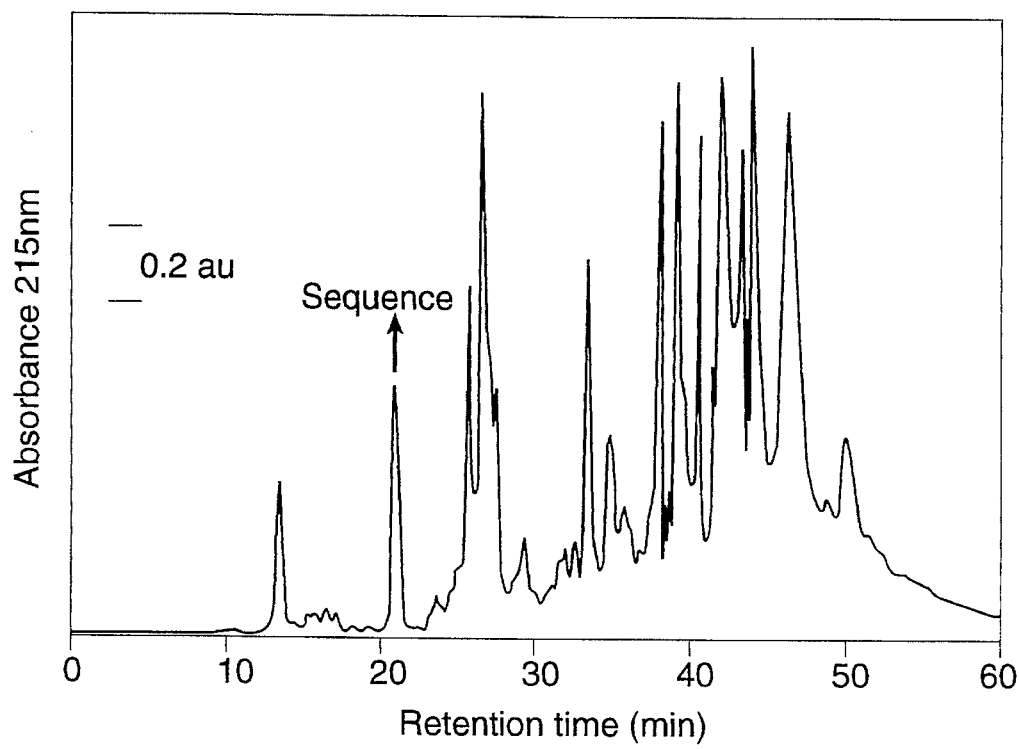
FIG. 13A presents a chromatogram for the active fraction and FIG. 13B shows the results of a mitogenic activity assay of LIM1215 cells.
Figure 13B:
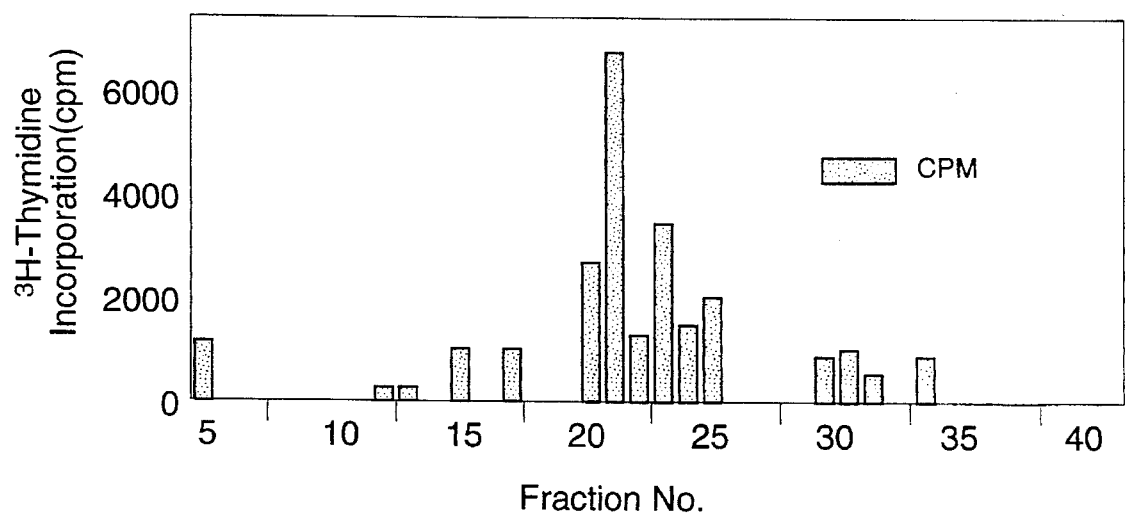
Figure 14B:
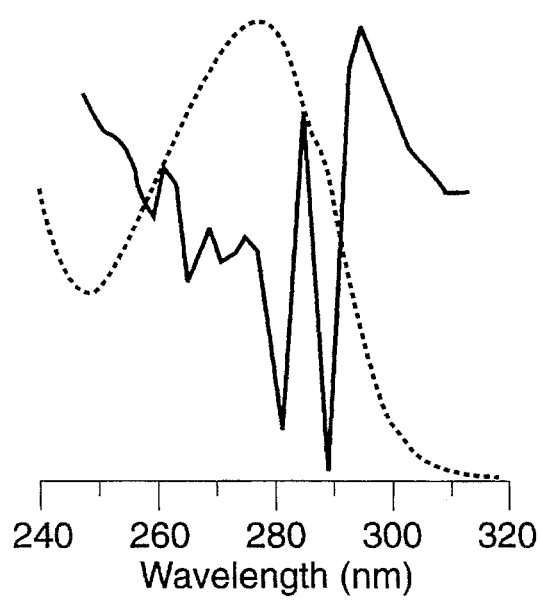
FIGS. 14A and 14B show results obtained using second derivative absorption spectroscopy.
Figure 14A:
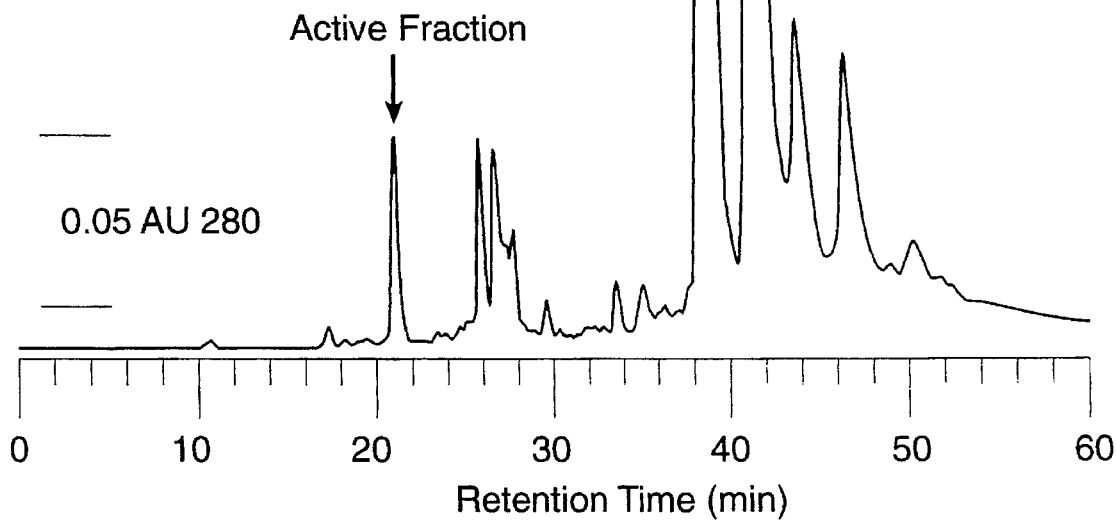

A chromatogram (215 nm), together with corresponding mitogenic activity on LIM 1215 cells is shown in FIGS. 13A and 13B. Fraction 21, which shows the major peak of mitogenic activity, coincides with the ultraviolet absorbing peak eluting at 20.9 minutes. Second derivative absorption spectrocopy identified a tryptophan residue from the minima characteristic of this amino acid, at 290±2 nm, as is shown in FIG. 14.

EXAMPLE 15

An aliquot of the peak discussed in example 14 was applied directly to the sample disc of an Applied Biosystems Model 470A gas phase sequencer, using Polybrene as a carrier. Sequencing was 5 carried out, revealing the following:

```
Lys Tyr Val Met Gly His Phe Arg Trp Asp Arg Phe Gly Arg Arg
              5                   12                   15

Xaa Gly Ser Ser Ser Ser Gly Val Gly Gly Ala Ala Gln
              20              25          28
```

(SEQ ID NO: 1). The initial yield was 114 picomoles. This material corresponds to a 28 amino acid residue stretch of amino acid corresponding to bovine pro-opiomelanocortin (POMC)$_{76-103}$, as per Nakanishi et al., Nature 278: 423–427 (1979). In turn, the sequence is equivalent to a lysine N-terminally extended form of the peptide known as $\ominus_3$MSH (Fenger et al., Biochem. J. 250: 781–788 (1988); Bateman et al., J. Biol. Chem. 265: 22130–22136.

Figure 15:
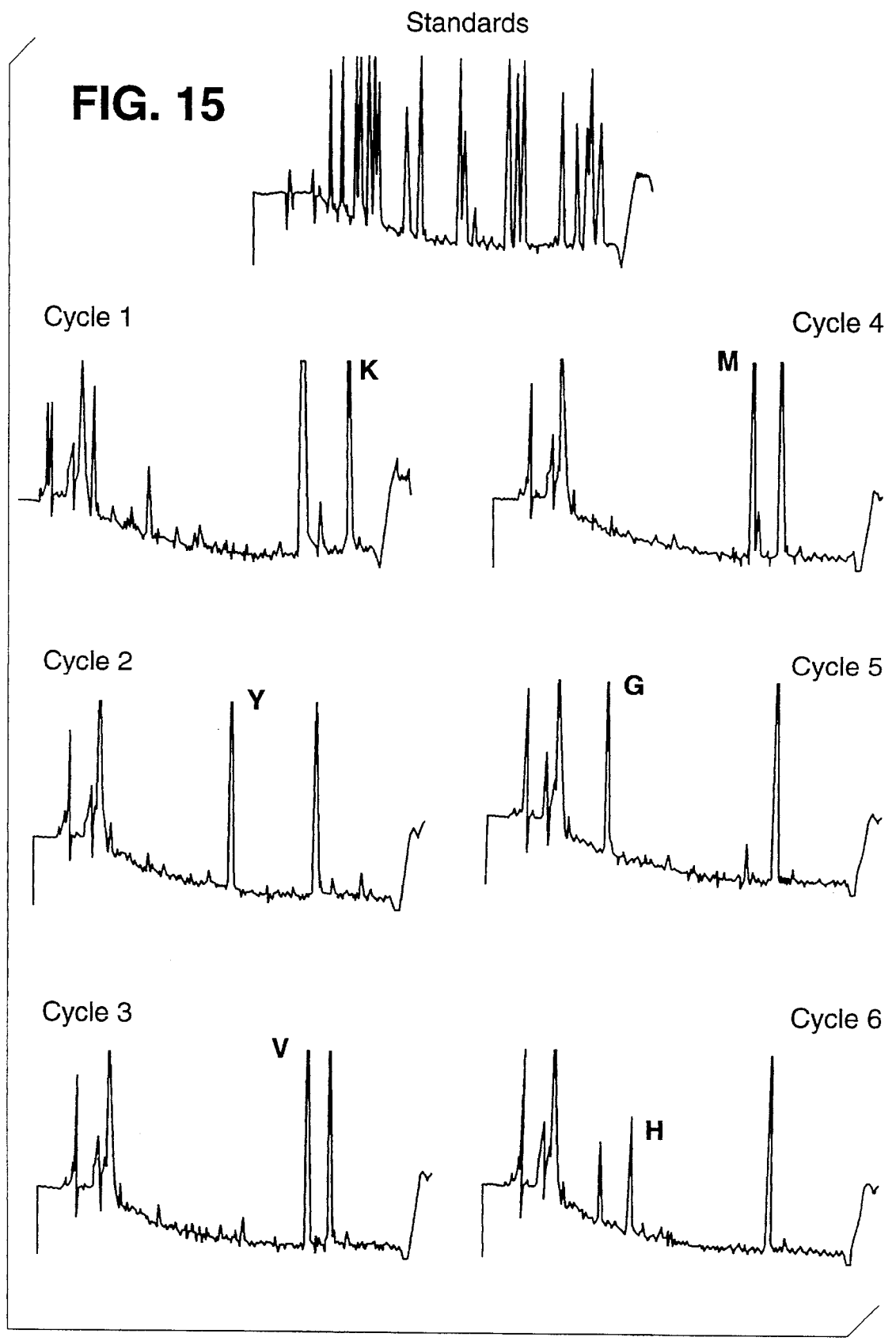
FIG. 15 presents RP-HPLC analysis of PTH amino acids obtained when analyzing the peptide.

Chromatograms illustrating RP-HPLC analysis of PTH amino acids generated at the first 6 cycles, together with corresponding PTH amino acid standards are shown in FIG. 15.

EXAMPLE 16

Figure 16A:
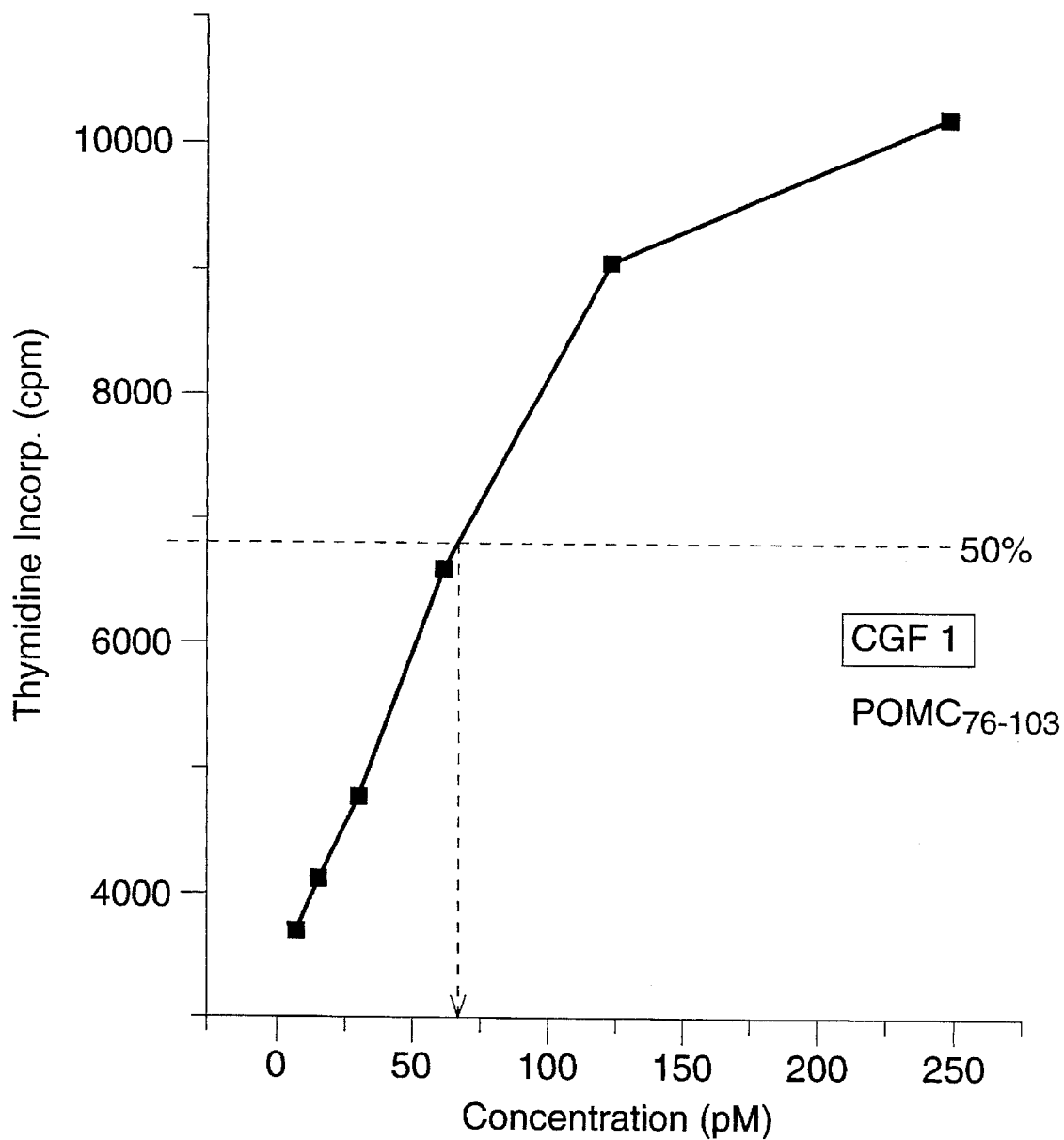
FIG. 16A shows the results of an assay where synthetic (POMC)$_{76-103}$ was tested as a mitogenic agent on colon cell line LIM 1215.
Figure 16B:
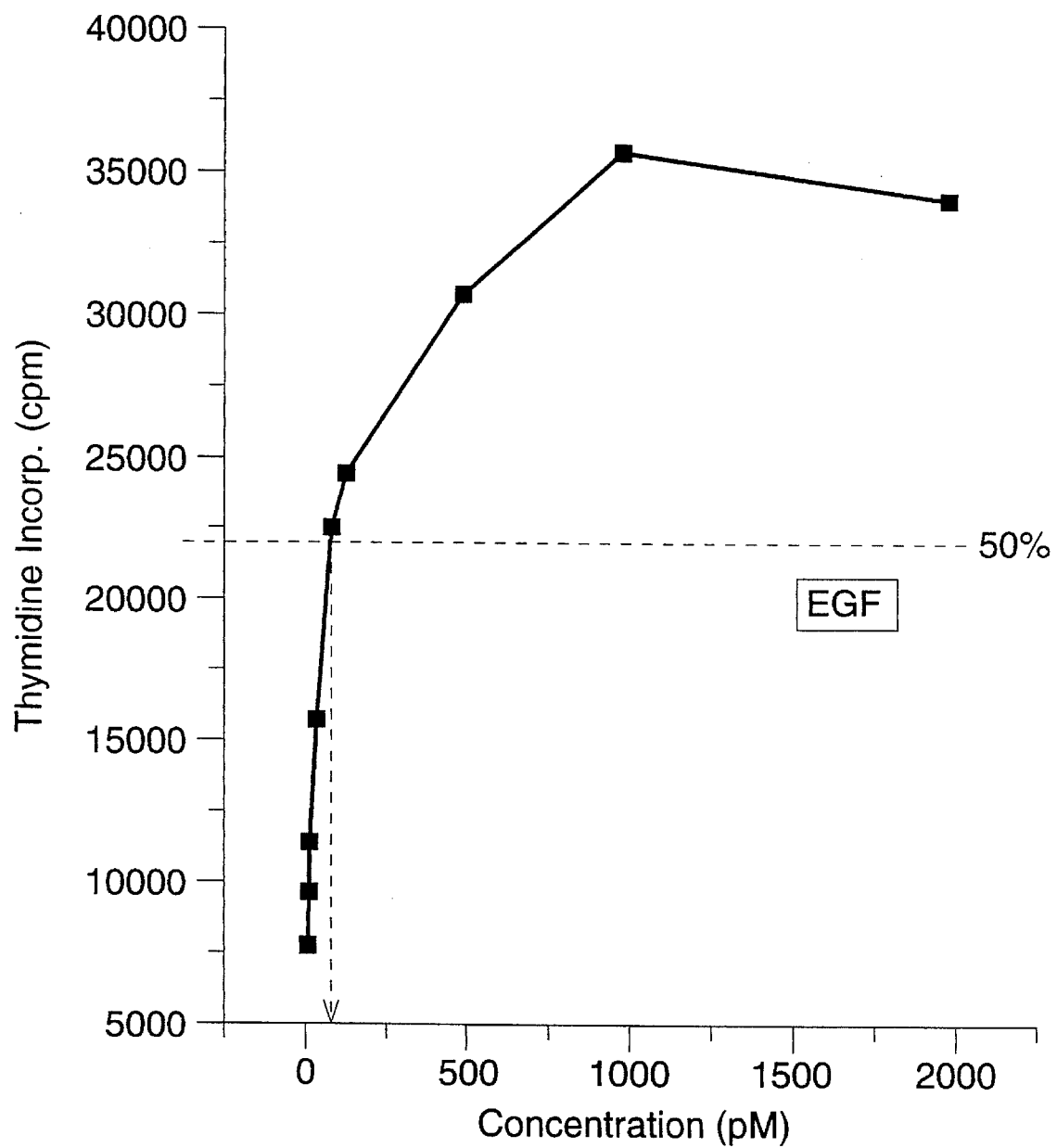
FIG. 16B shows results obtained using the same assay as was employed in 16A, but using epidermal growth factor (EGF).

The identification of the A2 peptide with (POMC)$_{76-103}$ suggests that the amino acid at position 16 is Asn. This is a potential glycosylation site. To determine if glycosylation was required for activity and to determine if the activity observed in A2 was properly attributed to the peptide rather than to some uncharacterized component, additional experiments were carried out using synthetic (POMC)$_{76-103}$. The material was synthesized, using art recognized techniques, and was then used in a mitogenic assay on LIM 1215 cells, following Nice et al., J. Biol. Chem. 266: 14425–14430 (1991), which is incorporated by reference in its entirety. The synthetic peptide was compared to EGF in the assay, the results of which are presented in FIGS. 16A (synthetic peptide), and 16B (EGF).

The synthetic peptide was seen to be biologically active, possessing a stimulation index approximately three fold (EC$_{50}$: approximately 75 pM). EGF is also active at this range (EC$_{50}$: 50 pM), but with 8 fold stimulation. The similar EC$_{50}$ values show that one may consider (POMC)$_{76-103}$ and EGF to be equipotent with respect to their effect on their target, i.e., colon cells.

EXAMPLE 17

The effect of the POMC$_{76-103}$, alone and combination with epidermal growth factor (EGF) was investigated. The peptide and recombinant human EGF ("rhEGF") were tested alone, and combined, in colony formation assays as described supra. The results, summarized below, are as follows:

| LIM 1215 Colony Stimulating Activity | |
|---|---|
| Substance | Colonies |
| POMC$_{76-103}$ (20 ng/ml) | 15, 20, 30 |
| rhEGF (10 ng/ml) | 300, 300, 320 |
| POMC$_{76-103}$ and rhEGF (20 ng/ml) (10 ng/ml) | 680, 770, 550 |

This effect is unexpected, and is well more than an additive effect.

The invention described herein and as exemplified by examples 13–17 will be seen to relate to a method for stimulating proliferation of certain cell types, such as colonic and intestinal cells, by administration of the peptide having the amino acid sequence set forth in SEQ ID NO: 1. This peptide, as has been pointed out, supra, is known, as it derives from bovine pituitary gland extract, however it is surprising that it has the cell proliferation stimulating effect it does. One would not connect pituitary extract with colonic cell stimulation. In addition, the effect of the peptide on colonic cells is greater than either of the other recognized colonic cell stimulating factors (EGF and bFGF), taken alone, and a mixture. Thus, it can clearly be said that the fact that POMC$_{76-103}$ has a superior cell proliferation effect on colon cells, is surprising.

Thus, one aspect of the invention relates to a method for stimulating proliferation of cells, such as colonic and intestinal cells, via application of the peptide POMC$_{76-103}$ (SEQ ID NO: 1) to the cells. Such application may be in vitro or in vivo. In the case of the latter, such application is appropriate, as the peptide of the invention derives from the ACTH molecule, and in vivo therapy with ACTH is well known. The therapeutic regime for treatment with the peptide and in accordance with the invention simply takes the form of administration of an effective amount of the peptide to a subject in need thereof. The effective amount will vary, although a dose of from about 0.1 ug to about 1.5 ug, where two doses are given per diem is preferred. An especially preferred regime will be one where the subject receives from about 0.25 ug to about 2.0 ug per diem, again, broken up into two applications per day.

When administered in vivo, it is preferable to target the peptide to the site where cell proliferation is desired. This targeting may be accomplished, e.g., by complexing the peptide to a targeting agent, such as a colon cell specific monoclonal antibody. An exemplary monoclonal antibody is A33, deposited in accordance with the Budapest Treaty at the American Type Culture Collection, 12301 Parklawn Drive, Rockville, Md, under ATCC designation HB8779. The initial deposit was made on Apr. 5, 1985. The complexing of the peptide to an antibody can be accomplished using art recognized techniques which need not be reiterated here.

The peptide, either alone or as the type of complex described supra, may be administered to a subject in connection with other agents which stimulate colonic cells, and/or other cells. Exemplary of such agents are the growth factors, including EGF and the FGFs, such as bFGF, the members of the interleukin family, especially those interleukins which stimulate proliferation of cell types such as platelets, and colony stimulating factors, such as G-CSF and GM-CSF. Interleukin 6, in particular, is known to exhibit megakaryocyte stimulating activity.

The administration of the described peptide and/or reagents containing it is useful for treatment of any colonic disorder where cell proliferation is necessary, and stimulation of the rate of proliferation is desirable. Non-limitative examples of such conditions are colonic ulcers, tissue trauma caused by infection, and Crohn's disease, although the artisan will be aware of others which fall under the broad rubrics elaborated upon supra.

Also embraced by the invention are reagents which consist essentially of the peptide described herein, and a second cell proliferation stimulating agent. Such reagents can be prepared in "one pot" form, or as reagent kits, e.g., where the two agents are kept separate, to be combined when administered. Such kits are characterized by two or more container means, each of which encloses a feature of the inventive kit, and a larger container means for holding all elements of the kit together.

The recognition that an indigenous peptide can be used for stimulating colonic cell proliferation suggests that disorders of the colon characterized by excess cell proliferation may involve a situation where the peptide acts as an autocrine growth factor. The invention thus also contemplates treating such autocrine disorders of the colon characterized by excess cell proliferation via administration of a specific inhibitor of the peptide, such as an antibody, a monoclonal antibody, or a binding antibody fragment which is specific to the peptide. Other features of the invention will be clear to the skilled artisan and need not be repeated here.

The terms and expressions which have been employed are used as terms of description and not of limitation, and there is no intention in the use of such terms and expressions of excluding any equivalents of the features shown and described or portions thereof, it being recognized that various modifications are possible within the scope of the invention.

We claim:

1. An in vitro method for stimulating proliferation of colonic cells, comprising applying to said colonic cells a composition consisting essentially of a peptide having SEQ ID NO: 1; wherein said composition is applied in an amount effective to stimulate colonic cell proliferation.

2. An in vitro method for stimulating proliferation of colonic cells, comprising applying to said colonic cells a composition consisting essentially of a peptide having SEQ ID NO: 1 and a growth factor; wherein said composition is applied in an amount effective to stimulate colonic cell proliferation.

3. The method of claim 2, wherein said growth factor is EGF or FGF.

4. The method of claim 2, wherein said growth factor is an interleukin.

5. The method of claim 4, wherein said interleukin stimulates proliferation of platelets.

6. The method of claim 2, wherein said growth factor is G-CSF or GM-CSF.

7. A method for stimulating proliferation of colonic cells, comprising administering to a subject in need thereof a composition consisting essentially of a peptide having SEQ ID NO: 1; wherein said composition is administered in an amount effective to stimulate colonic cell proliferation.

8. The method of claim 7, wherein said subject is a chemotherapy patient.

9. The method of claim 7, wherein said peptide is administered in an amount ranging from about 0.1 mg to about 2.5 mg per day.

10. A method for stimulating proliferation of colonic cells, comprising administering to a subject in need thereof a composition consisting essentially of a peptide having SEQ ID NO: 1 and a growth factor; wherein said composition is administered in an amount effective to stimulate colonic cell proliferation.

11. The method of claim 10, wherein said subject is a chemotherapy patient.

12. The method of claim 10, wherein said growth factor is EGF or FGF.

13. The method of claim 10, wherein said growth factor is an interleukin.

14. The method of claim 13, wherein said interleukin stimulates proliferation of platelets.

15. The method of claim 10, wherein said growth factor is G-CSF or GM-CSF.

* * * * *

UNITED STATES PATENT AND TRADEMARK OFFICE
CERTIFICATE OF CORRECTION

PATENT NO. : 5,547,940
DATED : August 20, 1996
INVENTOR(S) : Edouard C. NICE et al.

It is certified that error appears in the above-identified patent and that said Letters Patent is hereby corrected as shown below:

<u>column 8</u>, <u>line 49</u>, change "12" to - - 10 - -.

Signed and Sealed this

Fifteenth Day of August, 2000

Attest:

Q. TODD DICKINSON

*Attesting Officer*   *Director of Patents and Trademarks*

SEQUENCE LISTING ( 1 ) GENERAL INFORMATION:

( i i i ) NUMBER OF SEQUENCES: 1

( 2 ) INFORMATION FOR SEQ ID NO: 1:

( i ) SEQUENCE CHARACTERISTICS:
( A ) LENGTH: 28 amino acid residues
( B ) TYPE: amino acid
( D ) TOPOLOGY: linear ( i x ) FEATURE:
( A ) NAME/KEY: POMC76-103

( x i ) SEQUENCE DESCRIPTION: SEQ ID NO: 1:

```
Lys Tyr Val Met Gly His Phe Arg Trp Asp Arg Phe Gly Arg Arg Xaa
                  5                      10                     15
Gly Ser Ser Ser Ser Gly Val Gly Gly Ala Ala Gln
                 20                 25
```